(12) United States Patent
Pupek et al.

(10) Patent No.: US 8,921,611 B1
(45) Date of Patent: Dec. 30, 2014

(54) PROCESS FOR PRODUCING REDOX SHUTTLES

(75) Inventors: Krzysztof Z. Pupek, Plainfield, IL (US); Trevor L. Dzwiniel, Carol Stream, IL (US); Gregory K. Krumdick, Homer Glen, IL (US)

(73) Assignee: Uchicago Argonne, LLC, Chicago, IL (US)

( * ) Notice: Subject to any disclaimer, the term of this patent is extended or adjusted under 35 U.S.C. 154(b) by 411 days.

(21) Appl. No.: 13/446,072

(22) Filed: Apr. 13, 2012

(51) Int. Cl.
*C07C 41/01* (2006.01)

(52) U.S. Cl.
USPC .......................................... 568/648; 568/658

(58) Field of Classification Search
CPC ...................................................... C07C 41/01
USPC .................. 568/648, 658; 252/62.2; 429/188; 136/263
See application file for complete search history.

(56) References Cited

U.S. PATENT DOCUMENTS

| | | | | |
|---|---|---|---|---|
| 5,021,308 | A | * | 6/1991 | Armand et al. ................ 429/336 |
| 7,034,166 | B2 | * | 4/2006 | Tawada et al. ................. 549/469 |
| 2011/0294003 | A1 | | 12/2011 | Zhang et al. |

OTHER PUBLICATIONS

Common solvents for crystallization, obtained Aug. 12, 2011, http://ccc.chem.pitt.edu/wipf/Web/Crystallization%20Solvents.pdf., pp. 442 and 443.*

* cited by examiner

*Primary Examiner* — Rosalynd Keys
(74) *Attorney, Agent, or Firm* — Cherskov Flaynik & Gurda, LLC

(57) ABSTRACT

The invention provides a method for preparing 1,4-di-tert-butyl-2,5-bis(2-methoxyethoxy)benzene, the method comprising reacting 2,5-di-tert-butylbenzene-1,4-diol with cesium carbonate and halogenated ether in dimethyl formamide. The method yields 500 gram batches at a time, or multiples thereof. The method enables the industrial production of redox shuttles for use in lithium ion battery systems.

8 Claims, 2 Drawing Sheets

PROCESS FOR PRODUCING REDOX SHUTTLES

CONTRACTUAL ORIGIN OF THE INVENTION

The United States Government has rights in this invention pursuant to Contract No. DE-AC02-06CH11357 between the United States Government and UChicago Argonne, LLC representing Argonne National Laboratory.

BACKGROUND OF THE INVENTION

1. Field of the Invention

This invention relates to a method for producing large amounts of redox shuttle and more specifically, this invention relates to a method for producing at least one kilogram (kg) per batch of a redox shuttle having a first oxidation potential of approximately 4 volts (V).

2. Background of the Invention

Lithium-ion battery advances are the de facto power sources for portable electronic devices and vehicle propulsion. Rechargeable lithium-ion batteries are used for thousands of cycles with no gaseous exhaust, delivering high density energy and providing reliable and clean chemical energy storage. Compared to fossil fuels and biomass, lithium-ion batteries compare favorably in reducing air pollution and therefore global warming.

As lithium battery chemistry increases in voltage potential, so too does the need to prevent overcharging. One means for preventing overcharging is the use of electronic monitoring devices attached to each cell to monitor voltages.

Another means is the use of anti-overcharge additives to electrolyte. These additives include redox shuttle molecules. Generally, redox shuttle molecules can be reversibly oxidized and reduced at a defined potential slightly higher than the end-of-charge potential of the cathode. This mechanism can protect the cell from overcharge by locking the potential of the cathode at the oxidation potential of the shuttle molecules. Redox shuttles have been implemented for overcharge protection of 3 volts (V) class lithium-ion batteries.

Efforts have been made to provide redox shuttles with overcharge protections in excess of 4 V. See, for example U.S. Patent App. No. US 20011/0294003 A1, published Dec. 1, 2011, and incorporated herein by reference.

However, such state of the art shuttle production protocols result in extremely small yields (e.g., less than 10 grams). Also, those methods require inert environments and expensive, hazardous reagents.

Specifically, 1,4-di-tert-butyl-2,5-bis(2-methoxyethoxy) benzene has been previously used by the inventors as an effective redox shuttle. The bench chemistry of the production of the shuttle is depicted in Equation 1 below. The process for its production suffers from salient drawbacks, including the following:

- It requires a 17 hour reaction time;
- Only a 60 percent yield is realized;
- Hazardous feed materials are used, such as sodium hydride and peroxide-forming tetrahydrofuran;
- Inert, dry atmospheres are required inasmuch as anhydrous solvent is utilized;
- Hydrogen is generated as a side product and needs to be vented causing explosion hazard;
- The process produces a complex mixture requiring large volumes of solvents to separate the product. (For example, dichloromethane is used in the extraction, which is a highly toxic and persistent pollutant);
- Purification is via chromatography, which is lengthy and requires large amounts of solvents; and
- Initial batch size is less than 0.1 grams, which makes the process unsuitable for industrial scale-up.

Equation 1:

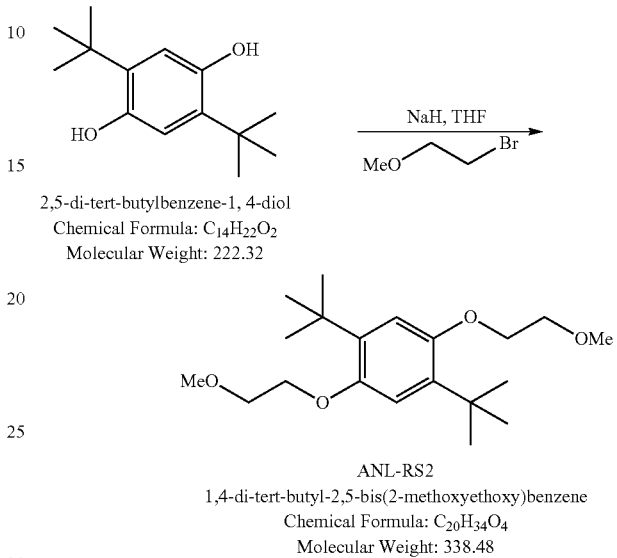

2,5-di-tert-butylbenzene-1, 4-diol
Chemical Formula: $C_{14}H_{22}O_2$
Molecular Weight: 222.32

ANL-RS2
1,4-di-tert-butyl-2,5-bis(2-methoxyethoxy)benzene
Chemical Formula: $C_{20}H_{34}O_4$
Molecular Weight: 338.48

A need exists in the art for a method for producing redox shuttles for use in batteries that yields multiples of 500 gram quantities per processing cycle. The method should not require elaborate processing parameters nor should the method require expensive and dangerous reagents. Also, the processing cycles should last no more than 6 to 8 hours.

SUMMARY OF INVENTION

An object of the invention is to provide production protocols of redox shuttles for use in rechargeable batteries that overcome many disadvantages of the prior art.

Another object of the invention is to provide a production protocol for 1,4-di-tert-butyl-2,5-bis(2-methoxyethoxy)benzene. A feature of the invention is that the protocol has a reaction time of between about 5 and 7 hours and a yield of approximately 80 percent. An advantage of the invented protocol is its utilization as a feedstock for industrial scale operations.

Another object of the invention is to provide a method for production of redox shuttles that enables one step batch production of the shuttles in access of 500 grams. A feature of the invention is the incorporation of a purification process which excludes the use of chromatography. An advantage of the invention is that the method can be conducted within 7 hours to produce industrial grade (greater than about 80 percent purity) redox shuttle material.

Still another object of the present invention is providing a method to produce a redox shuttle that can be conducted in open air. A feature of the method is the exclusion of highly flammable reagents and anhydrous reagents in the reaction liquor. An advantage of the method is that no cryogenic conditions, peroxidizable solvents, or halogenated solvents are utilized in the production of the shuttle.

Yet another object of the present invention is to provide a method for producing a redox shuttle without the need for a controlled atmosphere. A feature of the invention is that the reagents used are stable at ambient temperatures, pressures, and humidities. An advantage of the invention is its inherent safety inasmuch as the no flammable moieties or other secondary stream materials are generated during the production process.

Still another object of the invention is to provide an industrial scale process to produce redox shuttles having overcharge protection of approximately 4V. A feature of the process is its yield of the redox shuttle in 500 gram quantities per batch, or multiples thereof. An advantage of the invention is that industrial processes for the production of lithium ion battery electrolytes are easily facilitated.

Briefly, a method for preparing a redox shuttle is provided, the method comprising utilizing 2,5-di-tert butylbenzene-1, 4-diol in an alkylation reaction to create 1,4-di-tert-butyl-2, 5-bis(2-methoxyethoxy)benzene.

The invention also provides a method for preparing 1,4-di-tert-butyl-2,5-bis(2-methoxyethoxy)benzene, the method comprising reacting 2,5-di-tert-butylbenzene-1,4-diol with a base, in an aprotic dipolar solvent, and a compound capable of generating a leaving group. In embodiments of the invented process, the leaving group is a halide, or an alkyl sulfonate, or an aryl sulfonate, or combinations thereof. Suitable specific leaving groups are moieties selected from the group consisting of chloride, bromide, iodide tosylates, mesylates, brosylates, triflates, nonaflates, and combinations thereof.

Also provided is a method for preparing 1,4-di-tert-butyl-2,5-bis(2-methoxyethoxy)benzene, the method comprising reacting 2,5-di-tert-butylbenzene-1,4-diol with cesium carbonate and halogenated ether in dimethyl formamide.

BRIEF DESCRIPTION OF DRAWING

The invention together with the above and other objects and advantages will be best understood from the following detailed description of the preferred embodiment of the invention shown in the accompanying drawings, wherein.

DETAILED DESCRIPTION OF THE INVENTION

Figure 1:
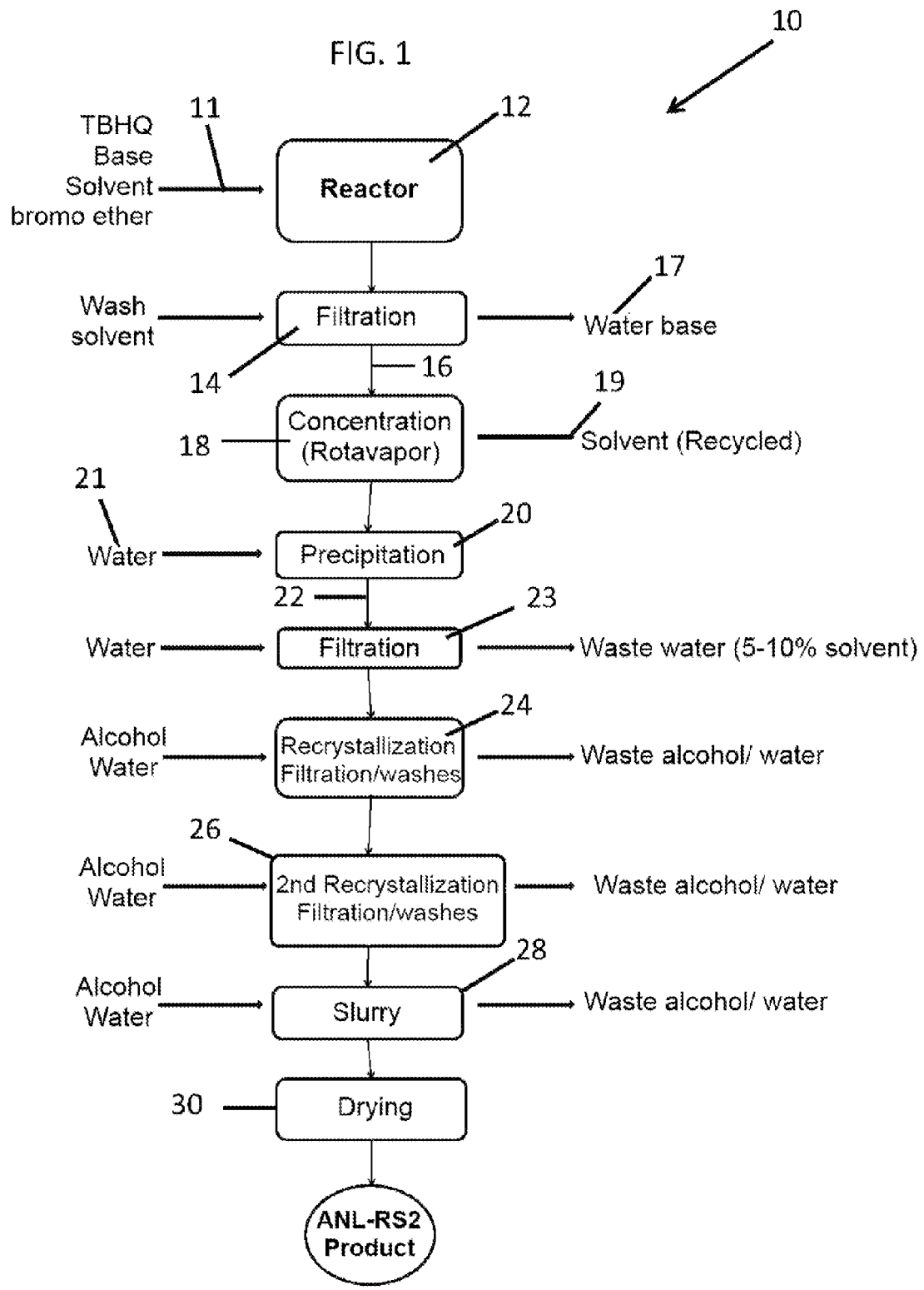
FIG. 1 is a flow chart for a process providing 1 kilogram yield of redox shuttle, in accordance with features of the present invention.

The foregoing summary, as well as the following detailed description of certain embodiments of the present invention, will be better understood when read in conjunction with the appended drawings.

As used herein, an element or step recited in the singular and preceded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

The invention provides a process for producing a high voltage reversible redox shuttle additive in bulk quantities exceeding 500 grams per batch. A feature of the additive is its incorporation of electron withdrawing groups.

The additive is 1,4-di-tert-butyl-2,5-bis(2-methoxyethoxy)benzene, having the chemical formula $C_{20}H_{24}O_4$.

The compound, having the "RS2" tradename, provides a means for protecting lithium-ion cells from overcharging by relegating the voltage exposure of the cathode of the cell to the oxidation potential of the shuttle. In an embodiment of the invention, the shuttles have redox potentials that are about 0.2 to 0.4 V higher than the positive electrode's maximum normal operating potential. Suitable cathode materials are those with maximum normal operating potentials of between approximately 3.8 and 4.2 volts. As such, suitable cathode materials include, but are not limited to, those comprised of $LiMn_2O_4$ and $Li_{12}Ni_{0.15}Co_{0.1}Mn_{0.55}O_2$.

The invented shuttle works in any electrolyte in which it has a solubility of at least about 0.1 M.

The invented process comprises an alkylation reaction using 2,5-di-tert-butylbenzene-1,4-diol as a starting material. A preferred embodiment of the invented process uses cesium carbonate and DMF to carry out this reaction. The chemistry of the preferred embodiment is depicted in Equation 2, below:

Equation 2:

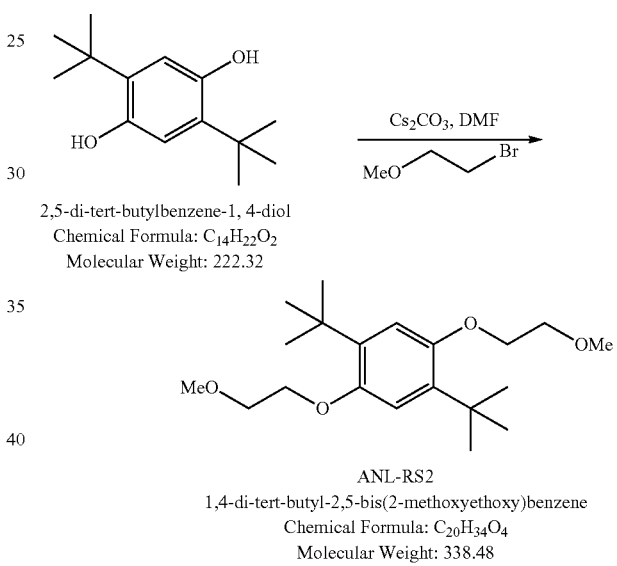

2,5-di-tert-butylbenzene-1, 4-diol
Chemical Formula: $C_{14}H_{22}O_2$
Molecular Weight: 222.32

ANL-RS2
1,4-di-tert-butyl-2,5-bis(2-methoxyethoxy)benzene
Chemical Formula: $C_{20}H_{34}O_4$
Molecular Weight: 338.48

The process depicted in Equation 2 supra is a preferred method for producing the shuttle, inasmuch as the carbonate reactant provides a basic moiety strong enough to initiate deprotonation of the hydroxyl groups on the butylbenzene. However, the moiety is weak enough to prevent destruction of the solvent. As such, bases with $pK_a$ of between approximately 8 and 14 are suitable. Those bases with $pK_a$ of between approximately 8 and 10 preferred and bases with a $pK_a$ of about 9 most preferred.

In an embodiment of the protocol, a carbonate-containing base coupled with an aprotic solvent provides a cornerstone of an industrial scale protocol for shuttle production. All metal carbonates such as those in periods 1 and 2 of the Periodic table (and commonly Li, Na, K, Mg, Ca, Cs etc.) will have essentially the aforementioned preferred $pK_a$. A specific mixture of disodium hydrogen phosphate/trisodium phosphate could have this range.

However, the inventors determined that the solubility of the base and/or the solubility of the metal hydroquinone salt is a further determining factor in the solubility of the shuttle residing in the electrolyte of the batter. Embodiments of the shuttle have a solubility in electrolyte of between about 0.05 M to 1 M, and preferably from 0.1 to 0.5 M.

Surprisingly and unexpectedly, the inventors found that $Cs_2CO_3$ base coupled with an aprotic solvent yielded purities of the shuttle above 99.9 percent with yields of about 80 percent. The purity, yield, and decreased production time of the shuttle which was obtained using the cesium carbonate base was unexpected in light of other basic moieties with a pKa of about 8 to 10, such as potassium carbonate and also sodium hydride, first auditioned by the inventors due to the relatively low cost of potassium and sodium compared to cesium. An intermediate (cesium salt of hydroquinone) is thought to be formed in the acid/base reaction, this intermediate having higher solubility and higher reactivity than the analogous sodium salt in THF. This higher solubility leads to a better rate of reaction and a shorter reaction time.

Solubility of the Cesium Base is Approximately 0.3 M.

The final product exhibiting relative para-positions of the ether groups confers high stability compared to those shuttles wherein the ether positions are on adjacent carbons or separated by only one carbon.

Alternative embodiments of the invented protocol are depicted below in Equations 3 and 4. The base used in these two protocols was sodium hydroxide. Suitable solvents for use in the Equation 3 and 4 protocols include tetrahydrofuran, 2-methyl tetrahydrofuran, toluene, benzotrifluoride, isopropyl acetate, methyl-tert-butyl ether and combinations thereof. "X" is any halogen or suitable leaving group.

Either the initial purity (93.5 percent in Equation 3) or the yield (65 percent in Equation 4) is not optimized compared to the protocol provided in Equation 2. This is because the crude product from protocols 3 and 4 contains more than the substantially single contaminant generated by the reaction produced using the chemistry depicted in Equation 2. Therefore, the protocols embodied in Equations 3 and 4 require additional purification steps, compared to the non-chromatography purification protocol of Equation 2.

Also, the protocol depicted in Equation 4 utilizes water miscible reactants (such as alkali metal hydroxides) which resulted in increased reaction times. The protocol in Equation 4 also utilizes phase transfer catalyst, such as benzyltriethylammonium, tetrabutylammonium, Aliquat (trioctylmethylammonium), benzyltrimethylammonium, tetraoctylammonium, where the counterion includes chloride, bromide, iodide, or hydroxide, and combinations thereof.

Notwithstanding the foregoing, all of the invented protocols (Equations 2-4) utilize relatively nonhazardous reagents compared to state of the art protocols.

Equation 3

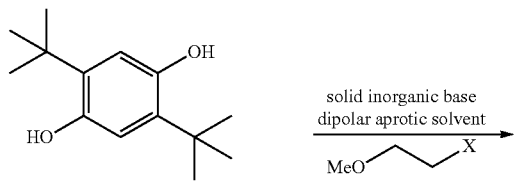

2,5-di-tert-butylbenzene-1, 4-diol
Chemical Formula: $C_{14}H_{22}O_2$
Molecular Weight: 222.32

-continued

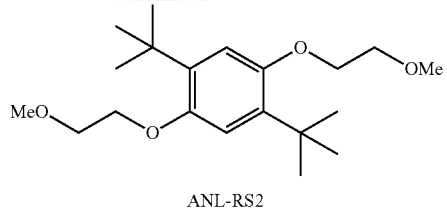

ANL-RS2
1,4-di-tert-butyl-2,5-bis(2-methoxyethoxy)benzene
Chemical Formula: $C_{20}H_{34}O_4$
Molecular Weight: 338.48

Equation 4

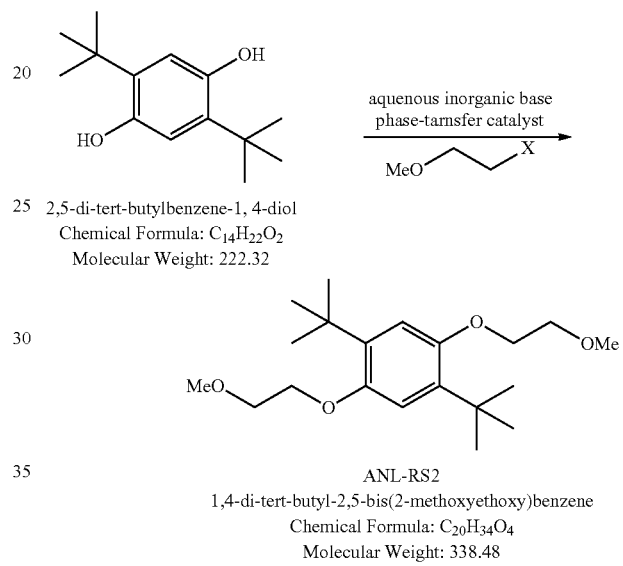

2,5-di-tert-butylbenzene-1, 4-diol
Chemical Formula: $C_{14}H_{22}O_2$
Molecular Weight: 222.32

ANL-RS2
1,4-di-tert-butyl-2,5-bis(2-methoxyethoxy)benzene
Chemical Formula: $C_{20}H_{34}O_4$
Molecular Weight: 338.48

Modifications of the bench protocol include the following:
1. Replacing the base NaH with a basic, poorly nucleophilic anion such as metal hydroxide or metal carbonate. Phosphates are also suitable. Carbonates (including those containing the metals sodium, potassium, lithium, and cesium) are preferred over hydroxides, and of the metal carbonates, cesium carbonate is preferred. This elimination of NaH in turn eliminated the evolution of hydrogen as a byproduct.
2. Replaced reaction solvent THF with DMF. Other suitable solvents include polar aprotic solvents include material selected from the group consisting of dimethyl acetamide (DMA), N-methylpyrrolidinone (NMP), dimethyl sulfoxide (DMSO), sulfolane, and combinations thereof.
3. Reaction time decreased from 16 hours to about 6-7 hours.
4. Work-up and isolation procedure changed from chromatography to recrystallization using isopropanol/water.
5. The extraction process using dichloromethane was eliminated.

An embodiment of the protocol resulted in an increase in yield to approximately 80 percent compared to a 60 percent yield under the old process. This, while keeping the exothermicity to 4 kiloJoules (kJ), and a rate of heat evolution to preferably about 600 Watts/Liter (W/L). The rate of heat evolution can vary widely however, given the efficiency of mechanical heat removal means such as chillers and condensers, the rate of introduction of reactants, or the combinations of these two factors.

A salient feature of the invented protocol is that there is no induction period or accumulation of reactants. Thus, the reaction is unlikely to develop a large concentration of reagents, which would otherwise cause a potentially hazardous rapid exothermic reaction upon initiation.

Figure 2:
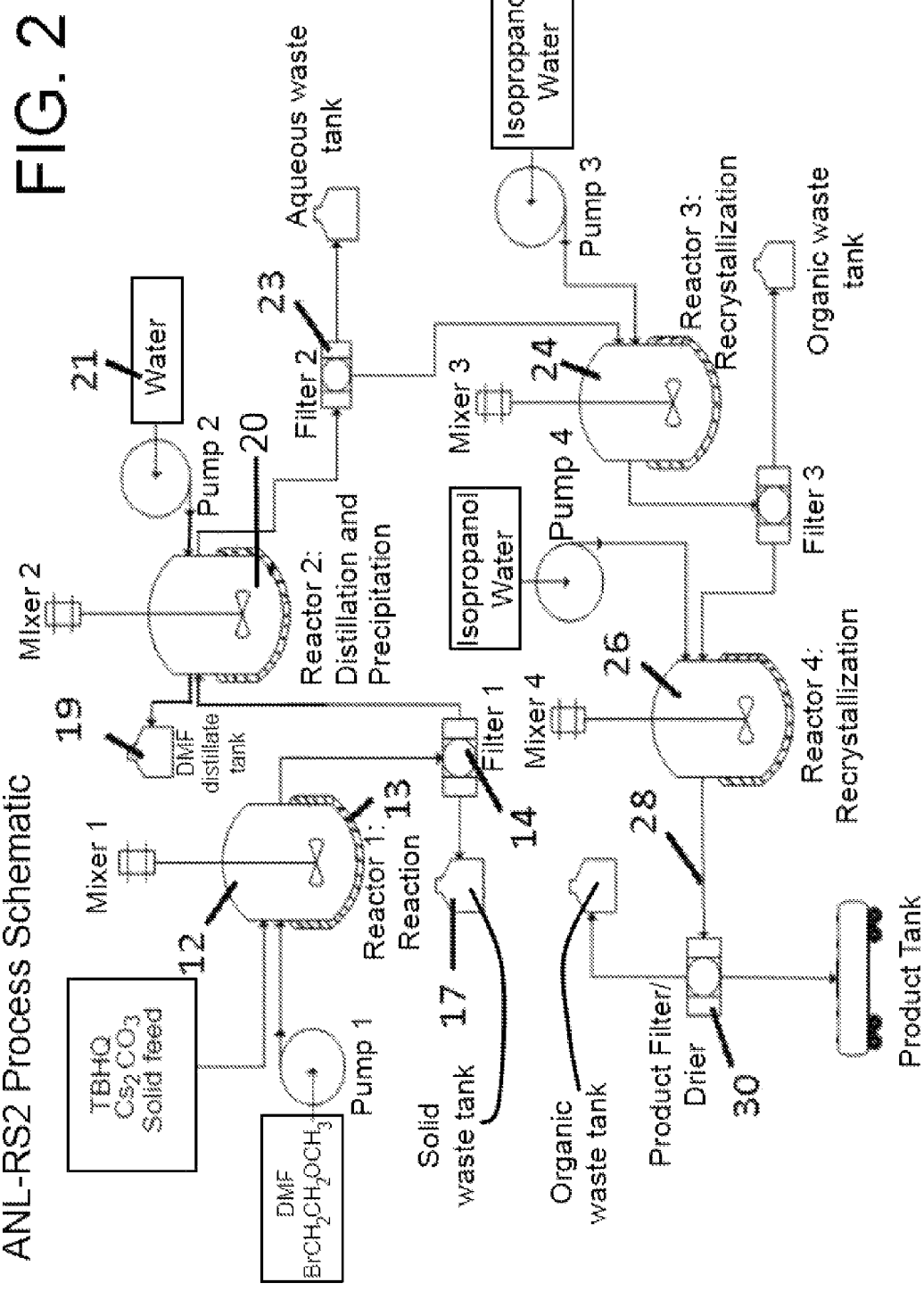
FIG. 2 is a process schematic of an embodiment of the invented batch-production method.

In an embodiment of the invented process, the redox shuttle is produced in approximately 500 gram batches, and multiples thereof (i.e., 500 grams, 1 kg, 1.5 kg, etc). FIG. 1 is a flow chart of this invented protocol, wherein approximately 1.6 kgs of the shuttle were produced. FIG. 2 is a process schematic of the embodiment depicted in FIG. 1.

Table 1 below provides an embodiment of the process associated with the chemistry depicted in Equation 2. The embodiment generates approximately 29 kilograms of 1,4-di-tert-butyl-2,5-bis(2-methoxyethoxy)benzene (RS2) utilizing a 400 liter reactor at approximately 85 percent capacity.

TABLE 1

Example 1 -- Process Parameters for RS2

| | Amount (kg) | Capacity (L) | Rate (L/h) | Temp (° C.) | RPM |
|---|---|---|---|---|---|
| Solid Feed 1: TBHQ | 25 | | | | |
| Solid Feed 1: Cs$_2$CO$_3$ | 108 | | | | |
| Pump 1: DMF | 200 | | | | |
| Pump 1: BrCH$_2$CH$_2$OMe | 47 | | 94 | | |
| Reactor 1 | | 400 | | 20-90 | |
| Mixer 1 | | | | | 0 to 125 |
| Filter 1 | | 100 | | | |
| Solid Waste tank | 131 | 100 | | | |
| Reactor 2 | | 400 | | 10-80 | |
| Mixer 2 | | | | | 0 to 150 |
| Pump 2: Water | 265 | | 530 | | |
| Filter 2 | | 50 | | | |
| Aqueous Waste 1 | 275 | 350 | | | |
| Reactor 3 | | 400 | | 10-90 | |
| Mixer 3 | | | | | 0 to 150 |
| DMF Distillate Tank | 190 | 250 | | | |
| Pump 3: Isopropanol | 157 | | 400 | | |
| Pump 3: Water | 130 | | variable | | |
| Filter 3 | | 50 | | | |
| Organic Waste Tank 1 | 297 | 350 | | | |
| Reactor 4 | | 400 | | 10-90 | |
| Mixer 4 | | | | | 0 to 150 |
| Pump 4: Isopropanol | 157 | | 400 | | |
| Pump 4: Water | 130 | | variable | | |
| Product Filter/Drier | | 50 | | 10-50 | |
| Organic Waste Tank 2 | 297 | 350 | | | |
| Product RS2 | 29 | | | | |

Table 1 provides specific weights and volumes of reactants, strictly for illustrative purposes. Rather, Table 1 should be construed as providing relative reagent amounts. For example, given an initial total weight of reactants of 380 kg, the weight percents of the TBHQ, Cs$_2$CO$_3$, DMF and BrCH$_2$CH$_2$OMe to the entire reaction mixture are about 6.5 percent, 28.5 percent, 52.5 percent and 12.5 percent, respectively. As such, product batch size can be doubled or tripled, etc., by multiplying these quantities by 2 or 3, etc. Generally, the inventors found that a constant in the invented protocol is that the amount of starting material (e.g. TBHQ) will yield substantially the same amount of the shuttle, such that 25-30 kgs of TBHQ will yield approximately 25-30 kgs of product. Suitable weight percents of the various reactants include, but are not limited to the following: TBHQ 4-10%, Cs$_2$CO$_3$ 10-40%, DMF 35-90%, and BrCH$_2$CH$_2$OMe 10-20%. Preferred ranges for the reactants include, but are not limited to, TBHQ 6-7%, Cs$_2$CO$_3$ 20-30%, DMF 40-60%, and BrCH$_2$CH$_2$OMe 12-15%.

The invented protocol is unique in that it provides a one-step process in the production of redox shuttles. One-step process is defined herein as a single chemical transformation, wherein a single feedstock compound is modified or reacted-upon to produce the desired shuttle. Additional purification and isolation procedures are part of the invented one-step transformation protocol.

A myriad of reaction atmospheres are suitable including, but not limited to, ambient atmosphere and pressure, inert atmosphere (e.g. argon, or nitrogen filled) and a combination thereof. In an embodiment of the protocol, inert atmosphere is employed during the initial reaction sequence (e.g. the reagent introduction step 11, FIG. 1) while ambient atmosphere and pressures are utilized for subsequent washing and purification procedures. A feature of the invented protocol is that substantially no anhydrous solvents are utilized.

The following detailed example elaborates on the flow charted protocol depicted in FIG. 1 designated as numeral 10. The protocol 10 generally embodies eight operations, the totality of which enable a single chemical transformation.

A salient feature of the invented protocol is that substantially all of the major reactants are added at the beginning of the process and homogenized in a single reaction chamber 12. A filtration step 14 follows to remove excess nucleophiles such as cesium carbonate. Base reagents, such as the carbonate or hydroxide, initially provide a means for deprotonating the hydroquinone feedstock, therefore producing a more reactive phenoxide anion. Filtration is utilized to remove the spent base reagents which are insoluble in the reaction mixture. (For example, when cesium carbonate is utilized as the base reagent, its subsequent reaction results in an insoluble mixture of cesium bromides and carbonates. Such precipitate needs to be removed from the liquor, either through filtration or with water. A more efficient embodiment of the protocol utilizes filtration instead of water.

In an embodiment of the invented process, the filtered liquor 16 is subjected to a means 18 for harvesting excess solvent, such as dimethylformamide (DMF), said means including, but not limited to a rotary evaporation process. This harvesting means is utilized in instances where the solvent is to be reused in efforts to minimize waste and lower cost. Generally, any means to drive off the solvent is suitable so as to form a concentrate. To the concentrate is added water in a precipitation step 20 in an amount to form a precipitate of the shuttle.

The precipitate 22 is then subjected to a plurality of recrystallization and washing steps 24, 26, and 28 wherein a mixture of water and alcohol is contacted with the shuttle to recrystallize, filter and wash the shuttle. A myriad of alcohols are suitable. Lower alcohols (C1-C3) are preferred, such as methanol, ethanol, 1-propoanol, 2-propanol, t-butanol, or any other water-miscible alcohol. Each step consists of recrystallization, filtration and washing of the precipitate. These purification steps continue until the shuttle attains a purity value appropriate for its end use. Suitable purity levels are at or greater than about 99.5 percent. These purity levels are attained as the invented process generates the shuttle with substantially only one impurity, as discussed infra. The filtration, evaporation and precipitation steps of the instant protocol need to deal with removal only of remaining original reactants, such as base and solvent, and base byproduct, to render a very pure (greater than about 95 percent) crude product. It is the lack of other impurities that allows this crude product to be crystallized to very high purity grades without the need for a prior clean up step using chromatography.

This contrasts with several different impurities being generated in state of the art protocols. State of the art protocols generate large amounts of impurities such that crude product from those protocols is less than 90-95 percent, which is too dirty for crystallization purification processes.

Generally, the efficiency of the process results in substantially only one impurity being present, that impurity being 1,4-di-tert-butyl-2-methoxy-5-(2-methoxyethoxy)benzene. Usually less than 0.1 percent of the impurity exists. This impurity does not impact battery performance. Purity can be determined by high performance liquid chromatography.

A drying step 30 is then implemented. The crystals are subjected to temperatures between approximately 20° C. and 50° C. for a time sufficient to substantially dry the product. At a residual moisture content of approximately 10 to 50 ppm, the product has an indefinite shelf life. In an embodiment of the invention, the crystals are subjected to temperatures of about 40° C. for a period of between about 12 and 120 hours. Large batches are substantially dry after approximately 24 hours of drying.

FIG. 2 is a process schematic of an embodiment of the invented batch-production method. A salient feature of the process, as depicted in FIG. 2, is a means for controlling reaction temperature so as to allow for generation of industrial sized (e.g. 500 grams) volumes of the shuttle. One such means is a chiller 13 in fluid communication with the reactor 12 so as to maintain the internal surfaces of the reactor 12 at a temperature sufficient to prevent volatilization of the solvents used in the process.

Another means to controlling reaction temperature is by controlling the rate of introduction of reactants which effect the overall rate of reaction. In an embodiment of the process, bromo ether is added in measured amounts so as to minimize the exothermicity of the process. Still another means to controlling reaction temperature is the combination of a mechanical means for removing heat, as discussed supra, and measured dosing of reagents. This combination enables the production of large batches of product in a minimal time period (e.g., within 6-7 hours).

Performance Detail

The scale-up batches of the batch produced shuttle show the same electrochemical performance as the bench-top samples. Both batches show very good overcharge protection. Area specific impedance of cells with and without RS2 show similar results during a 3C Hybrid Pulse Power Characterization (HPPC) test. Capacity fading was observed for cells containing the batch produced shuttle during normal cycles. High heat generation was observed during overcharge using Isothermal Micro calorimeter (IMC).

Testing parameters utilized the following electrolyte and electrodes:

Electrolyte: 0.25M (6.5 wt. %) batch shuttle in 1.2M $LiPF_6$ EC/EMC (3/7) (1500 g);
Electrolyte: 0.35M (9 wt. %) batch shuttle in 1.2M $LiPF_6$ EC/EMC (3/7) (100 g);
wherein EC is ethyl carbonate and EMC is ethyl methyl carbonate.
Cathode: LiFePO4 (SOC), LiFePO4/Carbon Black/Binder: 85%/7%/8%, Loading: 14.4 mg/cm$^2$.
Anode: SMG (Hitachi), SMG/Binder: 92%/8%, Loading: 8.2 mg/cm$^2$.

Example 1

An embodiment of the aforementioned process depicted in FIG. 1 follows:

A glass reactor (20 L, jacketed, Chemglass) equipped with drain valve, internal temperature probe, reflux condenser, gas inlet/outlet adapters and powder port was flushed with argon. The jacket of the reactor was connected to a mechanical means for controlling the interior surfaces of the reactor, such means including a heating/chilling circulator, such as a Huber 430. Aside from the use of thermal conduction as a means to control temperature, controlled addition of reactants can be utilized exclusively, or in combination with the mechanical thermal conduction means, as discussed supra.

The reactor was charged with DMF (12 L, BDH 111510D) and the stirring speed set to 120 rpm. 2,5-Di-tert-butylbenzene-1,4-diol (1,312 g, 5.90 mol, 1.0 eq, Aldrich MKBC8025V) was added followed by cesium carbonate (5,758 g, 17.67 mol, 3.0 eq, Alfa B09W012). The circulator was set to control the process (internal reaction mixture) temperature at about 60° C. A gradual addition of 1-bromo-2-methoxyethane was started when the reaction temperature reached about 58° C. The whole amount of the reagent (2,467 g, 17.748 mol, 3.0 eq, Oakwood B12M) was added over 20 minutes. The temperature of the reaction mixture spontaneously rose to 65° C. (exothermic reaction). The mixture was stirred for 1 h at 65° C. The circulator was set to about 70° C. The reaction was sampled after 5.5 h (time since addition of 1-bromo-2-methoxyetane was completed). HPLC analysis (Agilent Eclipse Plus, C18, ACN/water gradient elution, UV 225 nm) revealed complete consumption of the starting benzene-1,4-diol and formation of the desired product (96.52% by peak area integration).

The reaction mixture was cooled to about 20° C. The contents of the reactor were drained onto a filter (polypropylene filtration cloth, 61 cm diameter). The solids were washed with DMF (3 L). The combined filtrates were concentrated under reduced pressure on a Buchi rotary evaporator (R-215, bath temperature of about 70° C., pressure 10-14 mbar, vapor temperature 41-44 C). Thirteen liters of solvent (DMF) were recovered.

The 20 L reactor was cleaned and charged with water (14 L). The concentrate (5 L) was added to the stirred (120 rpm) water at room temperature over 10 minutes. The contents of the reactor were drained onto a filter (polypropylene filtration cloth, 61 cm diameter). The solids were washed on the filter with water (4 L) and air dried to yield 2,285 g of crude product. The combined filtrates were disposed as waste. The cleaned 20 L reactor was charged with the crude material. Isopropyl alcohol (7 L, BDH 11291002) was added to the reactor. The process temperature was set to about 55° C. and the stirring speed was set to 60 rpm. Complete dissolution of the solids occurred at about 37° C. Water (3.5 L) was added to the solution at about 52° C. over a period of 10 minutes. The Huber circulator was programmed to a cooling ramp of about 55° C. to 19° C. over 3 h. The solution was seeded with crystalline ANL-RS2 (2 g) at about 49° C.

The mixture was stirred 1 h at about 19° C. The contents of the reactor were drained onto a filter (polypropylene filtration cloth, 61 cm diameter). The material was air dried to yield 2,085 g of 1,4-di-tert-butyl-2,5-bis(2-methoxyethoxy)benzene. HPLC analysis (Agilent Eclipse Plus, C18, ACN/water gradient elution, UV 225 nm) revealed 99.46% purity of the desired compound. The material was re-crystallized from isopropanol/water (7 L/3 L) mixture in the same fashion as the first crystallization. The material from the second crystallization was suspended in 20 L reactor using isopropanol/water (5 L/5 L) mixture. The suspension was stirred about 2 h at about 20° C. The material was filtered off and dried first on air then in vacuum oven (10 mbar/40 C) until moisture content (monitored by coulometric KF titration) dropped below 20 ppm. Yield 1,582 g (79%) of 1,4-di-tert-butyl-2,5-bis(2-methoxyethoxy)benzene (ANL-RS2). Purity was greater than 99 percent (e.g., 99.92% for average HPLC peak area integration). Moisture was 13 ppm (average per KF coulometric titration).

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting, but are instead exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the terms "comprising" and "wherein." Moreover, in the following claims, the terms "first," "second," and "third," are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes, the present invention encompasses not only the main group, but also the main group absent one or more of the group members. The present invention also envisages the explicit exclusion of one or more of any of the group members in the claimed invention.

The invention claimed is:

1. A method for preparing a redox shuttle, the method comprising utilizing 2,5-di-tert-butylbenzene-1,4-diol in an alkylation reaction mixture to create 1,4-di-tert-butyl-2,5-bis (2-methoxyethoxy)benzene wherein the alkylation reaction is initiated with a base having a pKa of between about 8 and 10, wherein the base confers a solubility to a 2,5-di-tert-butylbenzene-1,4-diol salt in the mixture of at least about 0.1 M.

2. The method as recited in claim 1 wherein the base is solvated with a polar aprotic solvent.

3. The method as recited in claim 2 wherein the polar aprotic solvent is a material selected from the group consisting of dimethylformamide, dimethyl acetamide, N-methylpyrrolidinone), dimethyl sulfoxide, sulfolane, and combinations thereof.

4. The method as recited in claim 2 wherein the aprotic solvent is DMF.

5. The method as recited in claim 1 wherein the method requires no anhydrous solvent.

6. The method as recited in claim 1 wherein the redox shuttle is prepared in about 6 to 7 hours.

7. A method for preparing 1,4-di-tert-butyl-2,5-bis(2-methoxyethoxy)benzene, the method comprising reacting 2,5-di-tert-butylbenzene-1,4-diol with cesium carbonate and halogenated ether in dimethyl formamide.

8. The method as recited in claim 7 wherein the method occurs in ambient atmosphere.

\* \* \* \* \*

UNITED STATES PATENT AND TRADEMARK OFFICE
CERTIFICATE OF CORRECTION

| | | |
|---|---|---|
| PATENT NO. | : 8,921,611 B1 | Page 1 of 1 |
| APPLICATION NO. | : 13/446072 | |
| DATED | : December 30, 2014 | |
| INVENTOR(S) | : Krzysztof Z. Pupek, Trevor L. Dzwiniel and Gregory K. Krumdick | |

It is certified that error appears in the above-identified patent and that said Letters Patent is hereby corrected as shown below:

One the title page item (73), "Uchicago Argonne, LLC" should be -- UChicago Argonne, LLC --

In the Claims

Column 12, line 28, Claim 3, delete the ")" immediately after N-methylpyrrolidinone Signed and Sealed this
Twenty-first Day of April, 2015

Michelle K. Lee
*Director of the United States Patent and Trademark Office*